United States Patent [19]

Chen et al.

[11] Patent Number: 5,414,189
[45] Date of Patent: May 9, 1995

[54] ISOLATION OF HIGH PURITY DIAMONDOID FRACTIONS AND COMPONENTS

[75] Inventors: Catherine S. H. Chen, Berkeley Heights; Steven E. Wentzek, East Brunswick, both of N.J.

[73] Assignee: Mobil Oil Corporation, Fairfax, Va.

[21] Appl. No.: 111,222

[22] Filed: Aug. 23, 1993

Related U.S. Application Data

[63] Continuation-in-part of Ser. No. 933,799, Aug. 24, 1992, abandoned.

[51] Int. Cl.⁶ .......................... C07C 7/04; C07C 7/14
[52] U.S. Cl. ..................... 585/801; 585/812; 585/815
[58] Field of Search .................. 585/812, 815, 801

[56] References Cited

U.S. PATENT DOCUMENTS 3,944,626 3/1976 Honna et al. .................. 585/812

OTHER PUBLICATIONS

Aldrich Catalog (1991) by Aldrich Chemical Co. pp. 1724–1733.
Vogel, "Practical Organic Chemistry", 3rd Ed (1956) (Longman) pp. 108–122.

Primary Examiner—Asok Pal
Attorney, Agent, or Firm—Alexander J. McKillop; Dennis P. Santini; Robert B. Furr, Jr.

[57] ABSTRACT

A process is disclosed for separating high purity diamondoid fractions from a mixture containing substituted and unsubstituted diamondoid compounds.

4 Claims, 5 Drawing Sheets

DIAMANTANES FRACTION

FIG. 4B

ISOLATED DIAMANTANE IN HEPTANE

ISOLATION OF HIGH PURITY DIAMONDOID FRACTIONS AND COMPONENTS

CROSS REFERENCE TO RELATED APPLICATIONS

This application is a Continuation-in-Part of U.S. application Ser. No. 07/933,799, filed Aug. 24, 1992, now abandoned.

FIELD OF THE INVENTION

The present invention relates to a method for recovering high purity diamondoid fractions and components from a mixture containing substituted and unsubstituted diamondoid compounds.

BACKGROUND OF THE INVENTION

Many hydrocarbonaceous mineral streams contain some small proportion of diamondoid compounds. These high boiling, saturated, three-dimensional polycyclic organics are illustrated by adamantane, diamantane, triamantane and various side chain substituted homologues, particularly the methyl derivatives. These compounds have high melting points and high vapor pressures for their molecular weights and have recently been found to cause problems during production and refining of hydrocarbonaceous minerals, particularly natural gas, by condensing out and solidifying, thereby clogging pipes and other pieces of equipment. For a survey of the chemistry of diamondoid compounds, see Fort, Jr., Raymond C., *The Chemistry of Diamond Molecules*, Marcel Dekker, 1976, as well as U.S. Pat. Nos. 5,019,660 to Chapman and Whitehurst and 5,053,434 to Chapman.

In recent times, new sources of hydrocarbon minerals have been brought into production which, for some unknown reason, have substantially larger concentrations of diamondoid compounds. Some of these diamondoid mixtures cause severe plugging problems in downstream processing equipment. Other diamondoid mixtures remain in the liquid phase under natural gas processing conditions and can be easily removed in a liquid knockout drum.

The problem of diamondoid deposition and plugging in natural gas production equipment has been successfully addressed by a controlled solvent injection process. U.S. Pat. No. 4,952,748 to Alexander and Knight teaches the process for extracting diamondoid compounds from a hydrocarbon gas stream by contacting the diamondoid-laden hydrocarbon gas with a suitable solvent to preferentially dissolve the diamondoid compounds into the solvent. U.S. Pat. No. 5,016,712 to Cullick and Roach teaches a method for locating the solvent injection point within the natural gas wellbore.

Further studies have revealed that separating diamondoid compounds into high purity fractions is complicated by their overlapping boiling points and relatively high vapor pressures. U.S. Pat. Nos. 4,952,747, 4,952,749, and 4,982,049 to Alexander et al. teach various methods of concentrating diamondoid compounds which dissolved in a solvent for, among other reasons, recycling the lean solvent fraction for reuse, and each of these processes produces an enriched solvent stream containing a mixture of diamondoid compounds. While these techniques meet the industrial need for a constant supply of relatively lean solvent for continuous recycle, the diamondoid-enriched streams rejected by these processes are not sufficiently pure to themselves be commercially useful. As mentioned above, conventional distillation of diamondoid-containing solvent mixtures is complicated by the fact that diamondoid compounds exhibit vapor pressures which are unusually high for their molecular weights.

U.S. Pat. No. 5,120,899 to Chen and Wentzek, which is incorporated by reference as if set forth at length herein, teaches a method of recovering the total diamondoid mixture without contamination using a high boiling point solvent which is injected into the natural gas wellbore.

Thus it would be desirable to provide a method for separating these recovered diamondoid mixtures into high purity fractions and components.

SUMMARY OF THE INVENTION

This invention provides a method for separating high purity diamondoid fractions and components from a mixture of alkylated and non-alkylated diamondoid compounds. The steps of this invention are both counterintuitive and highly effective for separating high purity, high melting, unsubstituted diamondoids such as adamantane, diamantane, and triamantane from a complex mixture of substituted diamondoids.

In addition, removing higher melting fractions from the diamondoid mixture useful as a feedstock in this invention naturally lowers the freeze point of the resulting mixture, rendering the mixture more desirable as a component in a fuel or lubricant. The term "freeze point" as used herein refers to the highest temperature at which the liquid mixture precipitates solids from the mixture. Freeze point behavior has been studied extensively, particularly in the fields of jet and rocket engine fuels. In these applications, it is generally accepted that blending in a lower molecular weight solvent such as hexanes or heptanes will effectively lower the freeze point. Removing lower boiling fractions from the feedstock useful in the present invention, on the other hand, surprisingly causes no substantial increase in the freeze point, also has been found to beneficially depress the freeze point. This behavior runs counter to the industry practice of blending lighter fractions with heavier fractions to lower the freeze point of the resulting mixture. Further, the lower boiling components are useful as specialty chemicals and as feedstocks for pharmaceuticals.

The method of the invention comprises the steps of (a) providing a feed mixture of diamondoid compounds containing at least about 40 total weight percent substituted and unsubstituted adamantane, at least about 30 total weight percent substituted and unsubstituted diamantane, and at least about 5 total weight percent substituted and unsubstituted triamantane;

(b) distilling an overhead fraction from said feed mixture of diamondoid compounds, said overhead fraction characterized by an average carbon number which is lower than the average carbon number of said feed mixture, and having a freeze point which is higher than the freeze point of said feed mixture;

(c) cooling said overhead fraction to a temperature above the freeze point of said feed mixture; and (d) recovering unsubstituted diamondoid solids from said overhead fraction at a purity of at least about 90 weight percent.

In a preferred embodiment, the method further comprises recrystallizing the unsubstituted diamondoid solids obtained in the recovery step (d) in a suitable solvent such as hexanes or heptanes to a purity of at least about 99 weight percent.

The invention provides, in a second aspect, a method for separating high purity diamondoid fractions from a mixture of diamondoid compounds comprising the steps of:

(a) providing a feed mixture of diamondoid compounds containing unsubstituted adamantane, unsubstituted diamantane, unsubstituted triamantane, and substituted diamondoid compounds;

(b) distilling a first overhead fraction from said feed mixture, said first overhead fraction characterized by an average carbon number which is lower than the average carbon number of said feed mixture, wherein said first overhead fraction is further characterized by a higher freeze point than said feed mixture;

(c) cooling said first overhead fraction to recover unsubstituted adamantane from said cooled first overhead fraction in purity of at least about 90 weight percent;

(d) continuing said distillation to provide a second overhead fraction which upon cooling becomes a liquid and contains predominately a mixture of substituted adamantanes with each component having a higher carbon number than the unsubstituted adamantane and the mixture having a substantially lower freezing point than unsubstituted adamantane;

(e) distilling said feed mixture to provide a third overhead fraction, said third overhead fraction characterized by an average carbon number which is lower than the average carbon number of said feed mixture, wherein said third overhead fraction is further characterized by a higher freeze point than said feed mixture;

(f) cooling said third overhead fraction to recover unsubstituted diamantane from said cooled second overhead fraction in purity of at least about 90 weight percent;

(g) continuing said distillation to provide a fourth overhead fraction which upon cooling becomes a liquid and contains predominately a mixture of substituted diamantanes with each component of said mixture of substituted diamantanes having a higher carbon number than the unsubstituted diamantane and said mixture of substituted diamantanes having a substantially lower freezing point than unsubstituted diamantane;

(h) distilling a fifth fraction from said feed mixture, said fifth overhead fraction characterized by an average carbon number which is lower than the average carbon number of said feed mixture, wherein said fifth overhead fraction is further characterized by a higher freeze point than said feed mixture; and (i) cooling said fifth overhead fraction to recover unsubstituted triamantane from said cooled fifth overhead stream in purity of at least about 90 weight percent; and (j) recovering pot material containing a major amount of substituted triamantane and minor amounts of tetramantane and pentamantane.

In a preferred embodiment, the recovered pot material is percolated through a sorbent such as activated alumina or activated carbon to remove impurities such as color bodies and other polar compounds.

The diamondoid mixtures useful as feedstocks in the present invention may be solid, liquid, or a mixture of solid and liquid under ambient conditions, and useful feedstocks for the present process must contain at least some liquid. If the feedstock contains solids, it may optionally be filtered before the distillation stage, although this is not required. If the feedstock contains more than about 25 weight percent of diamondoid compounds which are normally solid under ambient conditions, the method of the invention preferably comprises an additional short-path distillation step in the absence of reflux, or filtration at ambient temperature to remove solids. For a general description of short-path distillation, see U.S. Pat. No. 5,120,899 to Chen and Wentzek, which is incorporated by reference as if set forth at length herein. If the feedstock contains less than about 25 weight percent of diamondoid compounds which are normally solid under ambient conditions, then the method may be carried out in a multistage distillation apparatus without the optional short-path distillation or filtration steps.

The method of the invention requires no additional concentration of the diamondoid fractions to precipitate the unsubstituted diamondoid solids.

EMBODIMENTS

Feedstocks

Figure 1:
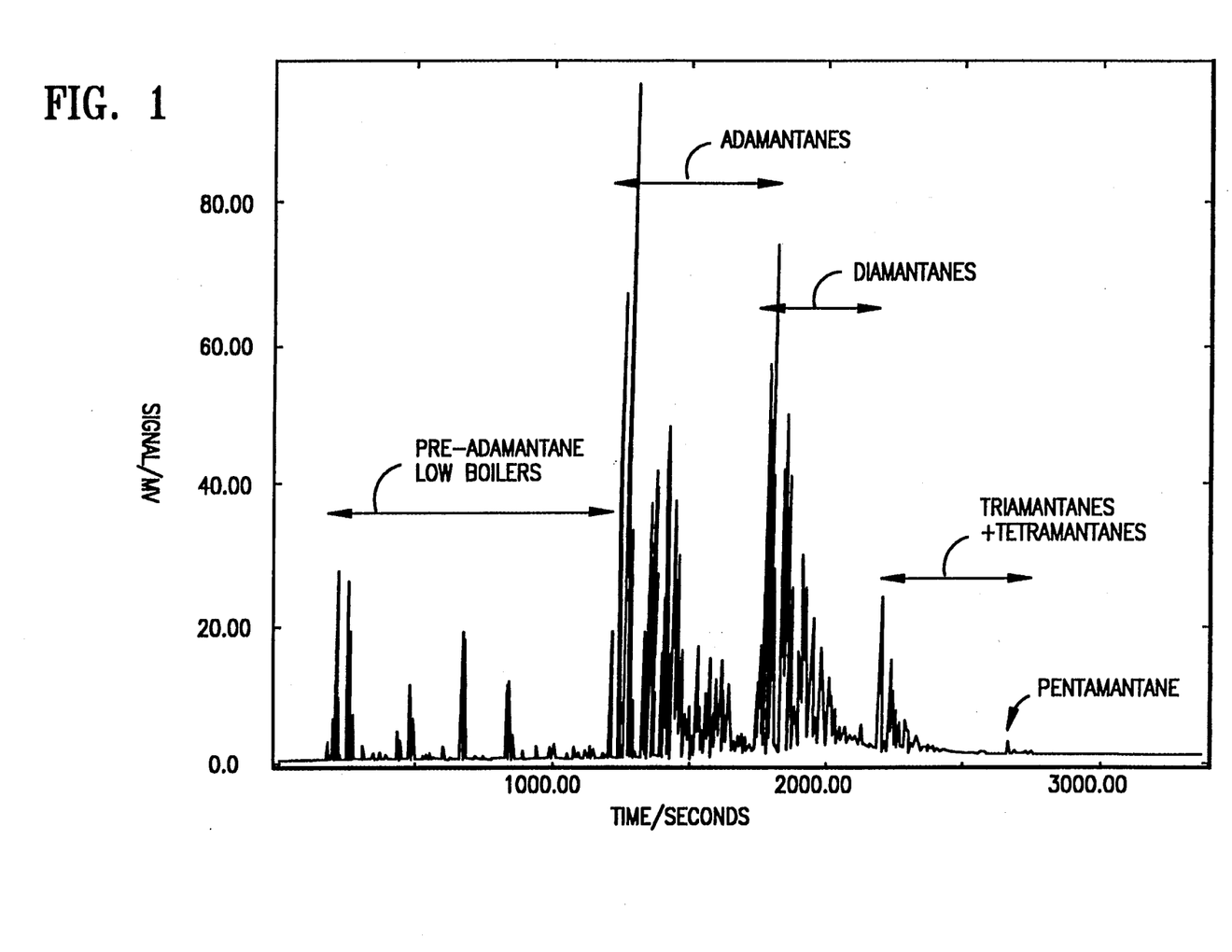
FIG. 1 is a gas chromatograph (capillary column) of a normally liquid mixture of diamondoid compounds including substituted adamantanes, unsubstituted adamantane, substituted diamantanes, unsubstituted diamantane, and triamantane.
Figure 2:
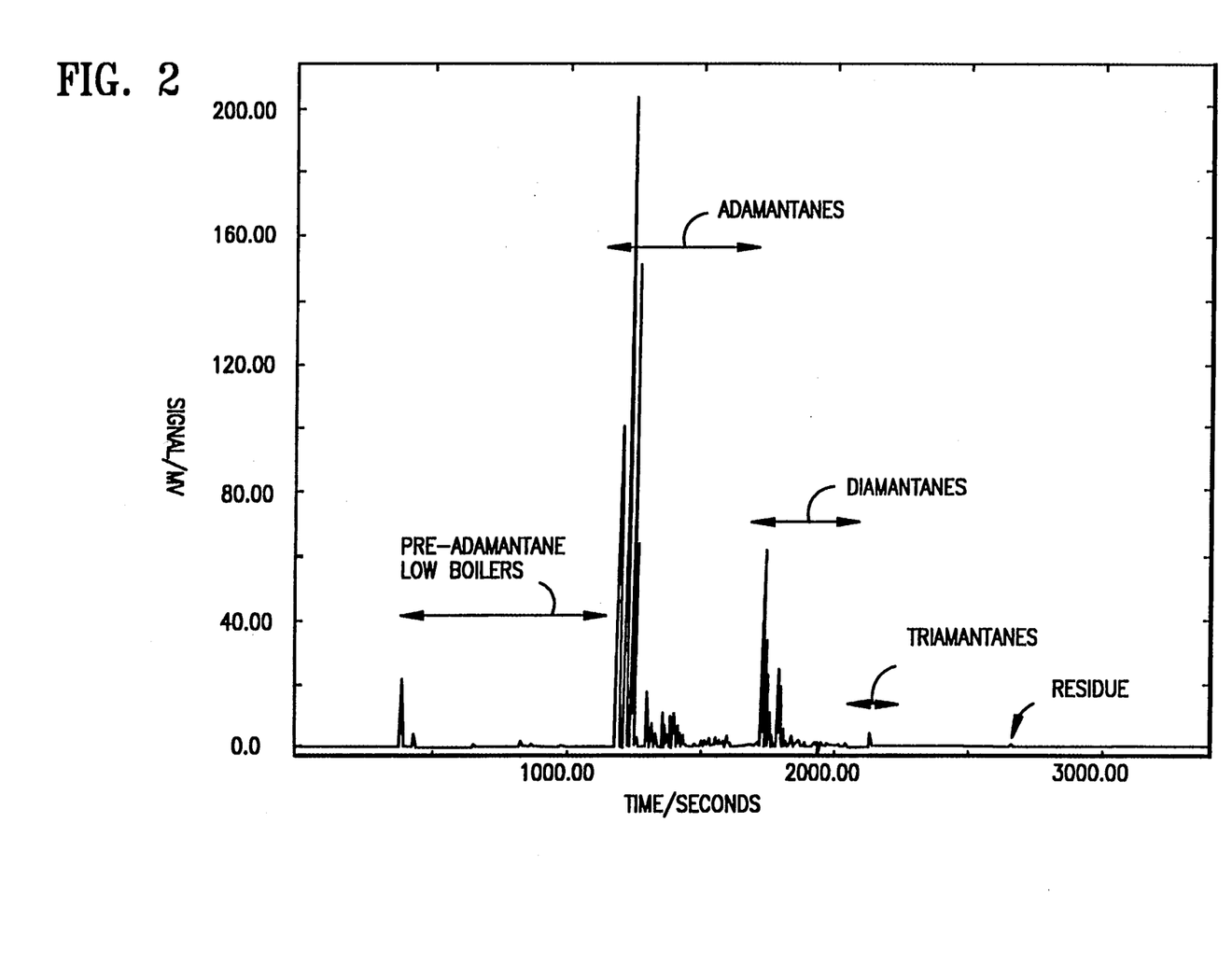
FIG. 2 is a gas chromatograph (capillary column) of a mixture of diamondoid compounds which contains both liquid and crystalline solids under ambient conditions.
Figure 3A:
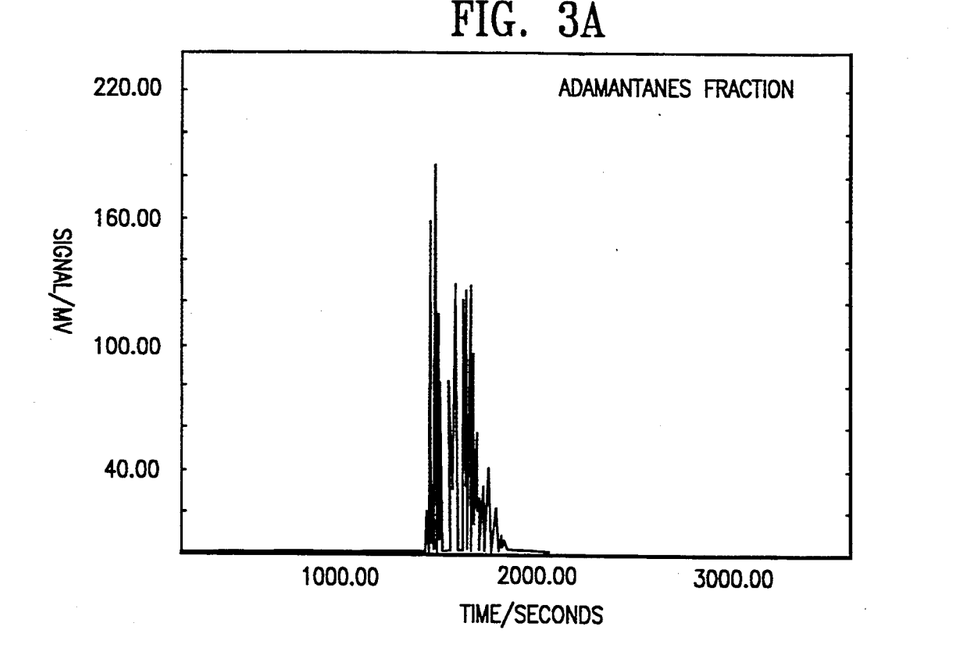
FIG. 3a is a gas chromatograph (capillary column) of the adamantanes fraction (including both substituted adamantanes and unsubstituted adamantane) of the normally liquid mixture of diamondoid compounds represented by the gas chromatograph of FIG. 1.
Figure 3B:
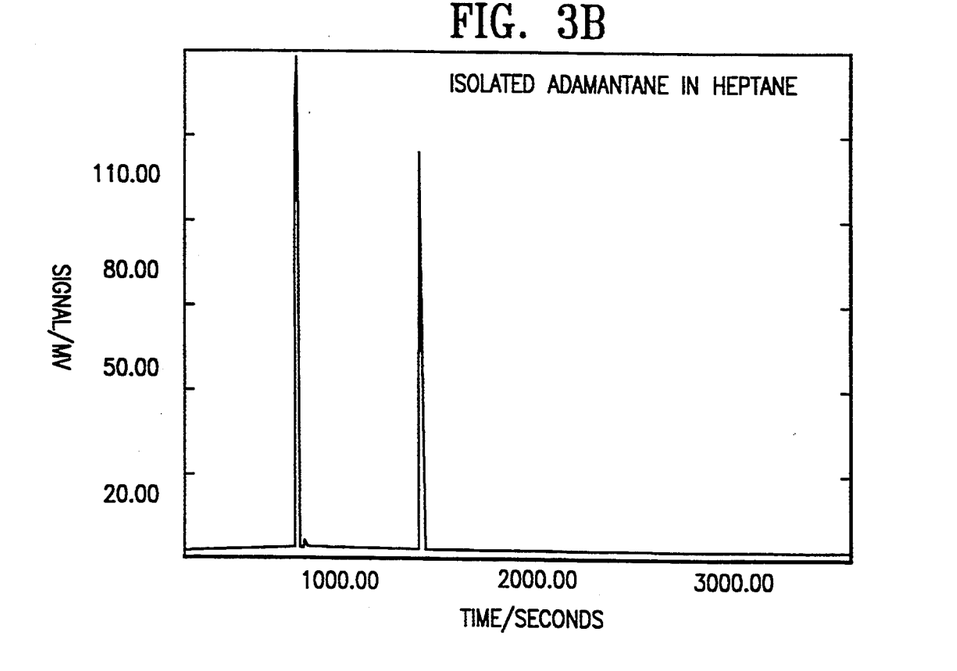
FIG. 3b is a gas chromatograph (capillary column) of adamantane in heptane. The adamantane was separated from the normally liquid mixture of diamondoid compounds represented by the gas chromatograph of FIG. 1 by the process of the present invention.
Figure 4A:
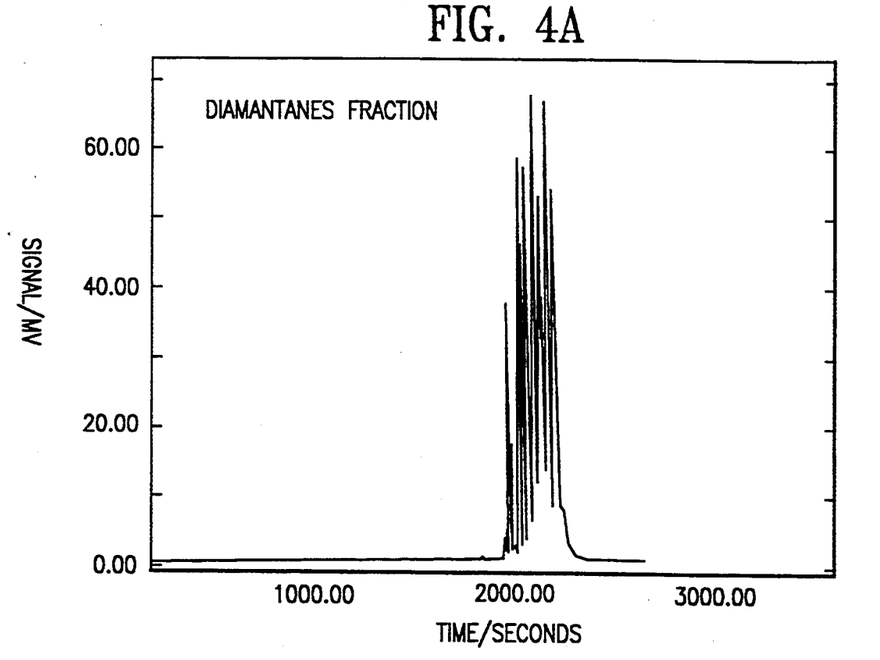
FIG. 4a is a gas chromatograph (capillary column) of the diamantanes fraction (including both substituted diamantanes and unsubstituted diamantane) of the normally liquid mixture of diamondoid compounds represented by the gas chromatograph of FIG. 1.
Figure 4B:
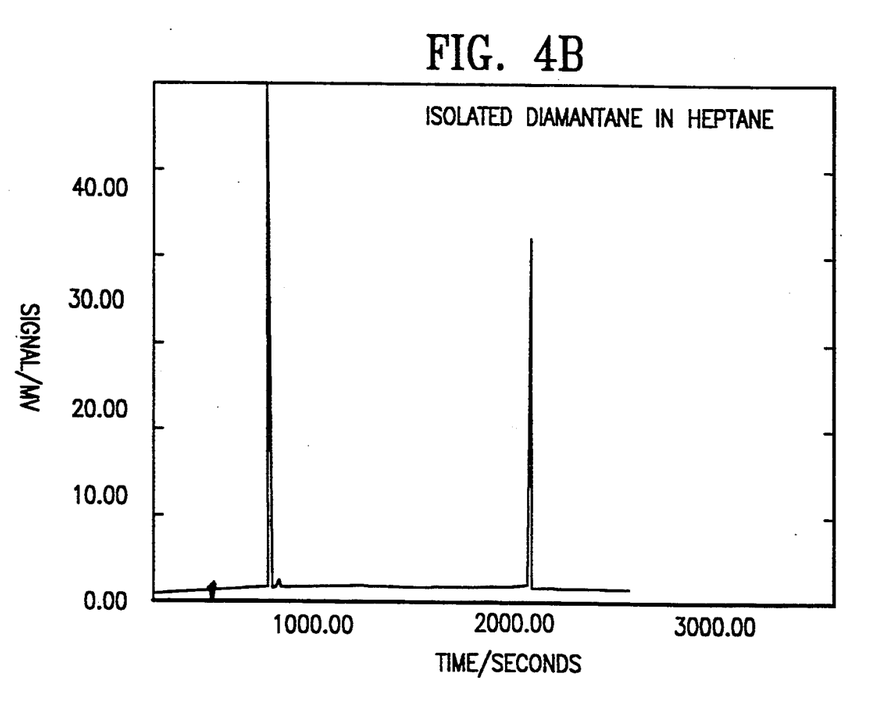
FIG. 4b is a gas chromatograph (capillary column) of diamantane in heptane. The diamantane was separated from the normally liquid mixture of diamondoid compounds represented by the gas chromatograph of FIG. 1 by the process of the present invention.
Figure 5A:
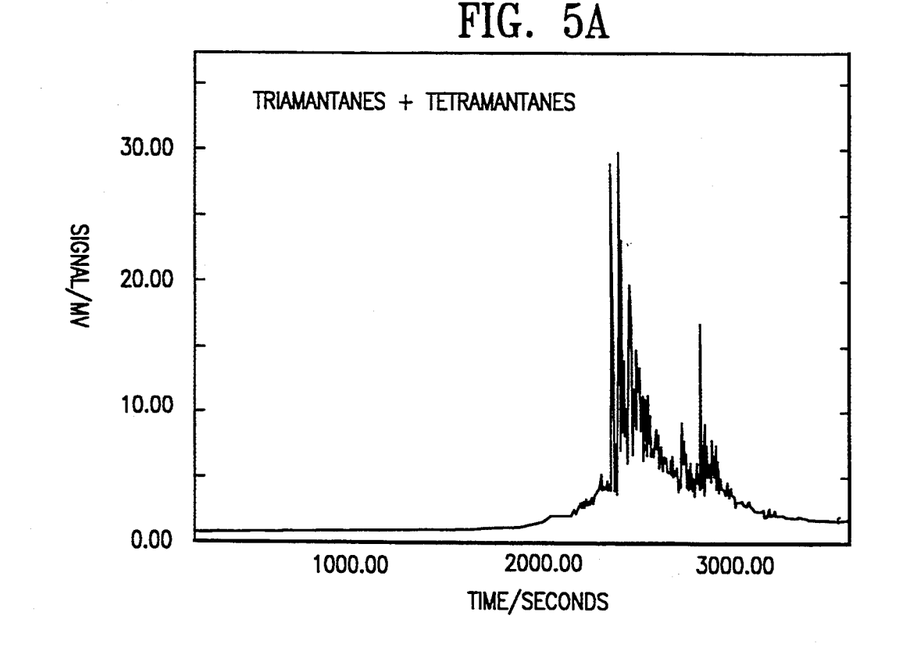
FIG. 5a is a gas chromatograph (capillary column) of the triamantanes and tetramantanes fraction (including both substituted and unsubstituted triamantanes and tetramantanes) of the normally liquid mixture of diamondoid compounds represented by the gas chromatograph of FIG. 1.
Figure 5B:
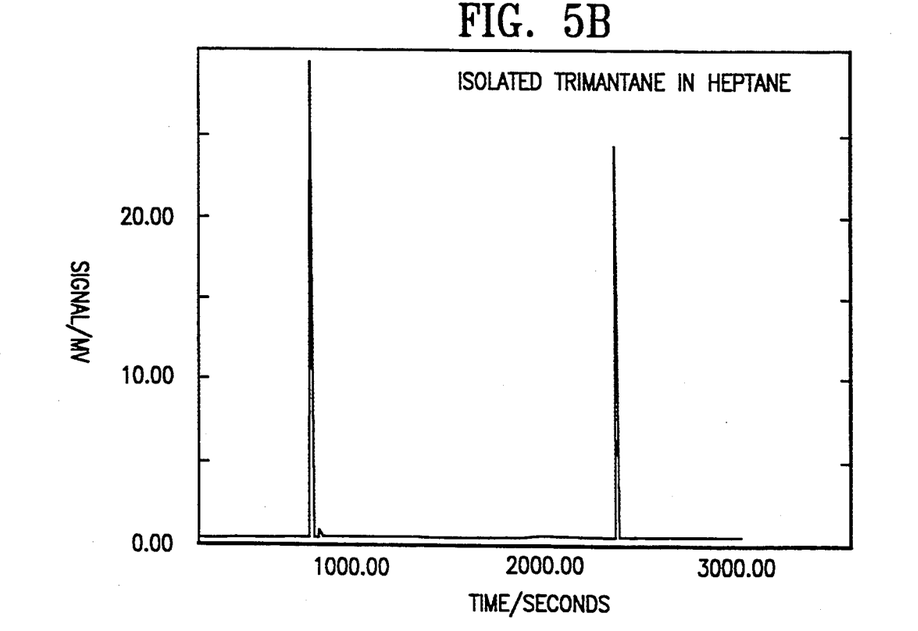
FIG. 5b is a gas chromatograph (capillary column) of triamantane in heptane. The triamantane was separated from the normally liquid mixture of diamondoid compounds represented by the gas chromatograph of FIG. 1 by the process of the present invention.

The feedstock composition is a critical aspect of the present invention. The feedstock must contain at least one unsubstituted diamondoid compound selected from the group consisting of adamantane, diamantane, and triamantane, together with one or more alkyl-substituted diamondoid compounds. FIG. 1 shows a gas chromatograph of a normally liquid mixture of diamondoid compounds useful as a feedstock in the present invention, which mixture includes unsubstituted adamantane, substituted adamantanes, unsubstituted diamantane, substituted diamantanes, unsubstituted triamantane, substituted triamantane, as well as tetramantanes and pentamantanes in minor quantities.

The preferred processing steps in the method of the invention depend upon the content of normally solid diamondoid compounds in the feedstock. If the feedstock contains more than about 25 weight percent of diamondoid compounds which are normally solid under ambient conditions, the method of the invention preferably comprises an additional short-path distillation step in the absence of reflux, or filtration at ambient temperature to remove solids. If the feedstock contains less than about 25 weight percent of diamondoid compounds which are normally solid under ambient conditions, then the method may be carried out in a multistage distillation apparatus without the optional short-path distillation or filtration steps. Examples of feedstocks which are preferably filtered at ambient or lower temperature or which are preferably distilled in a short-path distillation apparatus prior to multistage distillation are shown below in Examples 8 and 9.

Fractional Separation

The present invention maybe carried out (a) in a short path distillation apparatus without reflux followed by (b) a multiple stage distillation apparatus, if the feed mixture contains a large amount (i.e. 25 wt % or more) of unsubstituted diamondoids. If the feed contains less than about 25 wt % unsubstituted diamondoids, the invention may be carried out without the initial short-path distillation step.

The diamondoid-containing feed may suitably be charged to a distillation vessel under vacuum conditions ranging from about 0.05 to about 25 Torr, preferably from about 0.1 to about 10 Torr, most preferably from about 0.2 to about 2 Torr. The distillation is appropriately conducted in a vessel rated for full vacuum service under the operating temperature selected from the range of about 0° C. to about 150° C. The distillation vessel useful for the optional short-path distillation step is preferably connected to a receiver by heated lines of relatively large diameter to avoid condensation or sublimation of valuable products before the products reach the receiver. The separation steps of the present invention may be conducted in batch or continuous mode.

The distillation vessel useful for the optional short-path distillation step may, for industrial applications, more particularly comprise a flash drum rated for full vacuum service at the feedstock endpoint temperature. In one laboratory embodiment, the short-path distillation/crystallization stage may be conducted in a Kugelrohr apparatus as described below in the Examples. For example, a vessel equipped with suitable heating means, such as external or internal steam or electric heating coils and a temperature controller would be a useful distillation vessel. The vessel preferred for industrial applications of the multistage distillation of the invention contains one or more sections of distillation trays or packing.

To initiate the separation process step in the preferred batch mode, the distillation vessel is filled with diamondoid-containing feed and the temperature is raised incrementally and pressure is decreased until a vapor product flow is detected, at which point the temperature and pressure are held constant until the vapor product flow ceases. The pot temperature is then raised and/or the pressure is decreased to continue separation.

The distillation step of the invention produces at least two fractions which are enriched in diamondoid compounds having a single backbone structure. As used herein, the term "backbone structure" refers to the structure of the unsubstituted diamondoid homologs, which include adamantane, diamantane, triamantane, tetramantane, and pentamantane. Thus adamantane and any adamantane derivative which can be made by substituting a functional group (or groups) for at least one hydrogen of the unsubstituted adamantane share a single backbone structure. Examples of substituent groups include alkyl, aryl, and halogens, merely to name a few. For example, a fraction enriched in diamondoid compounds having the backbone structure of adamantane would contain a major portion of adamantane and various alkyl substituted adamantanes, such as methyl- and ethyl-substituted adamantanes. On the other hand, a fraction enriched in diamondoid compounds having the backbone structure of diamantane would contain a major portion of diamantane and various substituted diamantanes, for example, alkyl-substituted diamantanes such as the methyl- and ethyl-substituted diamantanes.

Surprisingly, it has been found that crystalline solids of substantially pure adamantane, diamantane, or triamantane were readily obtained in overhead fractions prior to substituted adamantane, diamantane, or triamantane, respectively. After these solids are collected from the cooled overhead stream, the liquid portions of the diamondoid fractions may be optionally be further purified by repeating the distillation and sublimation steps of the invention. The liquids may be distilled individually or may be recombined before charging the mixture to the distillation/sublimation stage of the invention.

In a preferred embodiment, this invention separates a mixture of substituted and unsubstituted diamondoids into at least one liquid fraction and one solid fraction, and typically produces about three liquid fractions and three solid fractions. The solids produced by the distillation/sublimation stages are of unusually high purity, typically exceeding 90 to 95 weight percent purity.

For feedstocks containing less than about 25 weight percent diamondoid compounds which are normally solid under ambient conditions, the method of the invention is preferably conducted in a suitable multi-stage distillation tower. Tower temperature must be carefully controlled to avoid sublimation of solids in the upper tower and overhead conduit. The temperatures in the overhead condenser and reflux lines must be carefully controlled to avoid plugging the conduit with crystalline materials. One example of a multi-stage distillation tower useful in the distillation/sublimation stage of the invention is an ASTM D-2887 distillation unit as described below in Example I with the addition of supplemental temperature controllers in the upper tower sections and overhead conduit to avoid plugging.

Table 1, below, illustrates three diamondoid mixture useful as feedstocks in the present invention. Mixture A contains adamantanes, diamantanes, and triamantanes. Mixture B contains diamantanes and triamantanes. Mixture C contains adamantanes with trace amounts of higher molecular weight diamondoids.

TABLE 1

Examples of Useful Diamondoid-Containing Feedstocks (wt. %)

| Compounds | A | B | C |
|---|---|---|---|
| adamantane | 1.364 | none | 1.234 |
| 1-methyl adamantane | 5.615 | none | 7.617 |
| 1,3-dimethyl adamantane | 6.070 | none | 10.174 |
| 1,3,5-trimethyl adamantane | 2.438 | none | 4.796 |
| 1,3,5,7-tetraamethyl adamantane | 0.413 | none | 0.713 |
| 2-methyl adamantane | 1.003 | none | 1.754 |
| t-1,4-Dimethyl adamantane | 1.514 | none | 2.980 |
| c-1,4-Dimethyl adamantane | 1.516 | none | 3.459 |
| 1,3,6-Trimethyl adamantane | 1.774 | none | 4.083 |
| 1,2-Dimethyl adamantane | 1.483 | | 3.368 |
| 1r, 3,4t-Trimethyl adamantane | 2.056 | | 4.647 |
| 1r, 3,4c-Trimethyl adamantane | 2.117 | | 4.898 |
| 1,3,5,6-tetramethyl adamantane | 2.044 | | 5.308 |
| 1-ethyl adamantane | 0.630 | | 1.523 |
| 2,6-; 2e,4e-; 2e,4a-diMe Ad | 0.118 | | 0.285 |
| 1,2,3,5-tetramethyl | 0.07 | | 0.17 |
| 1-ethyl-3-methyl adamantane | 2.16 | | 5.17 |
| 1,2,3-Trimethyl adamantane | 0.34 | | 0.81 |
| 1-ethyl-3,5-dimethyl adamantane | 1.582 | 0.012 | 3.909 |
| 1-ethyl-3,5,7-trimethyl adamantane | 0.424 | | 1.031 |
| 1,2,3,5,7-pentamethyl adamantane | 1.050 | 0.029 | 2.489 |
| Other adamantanes | 14.432 | 6.631 | 23.083 |
| Total adamantanes | 50.213 | 6.672 | 93.501 |
| Diamantane | 3.967 | 5.560 | 1.342 |
| 4-Methyl-diamantane | 5.345 | 8.338 | 1.522 |
| 4,9-Dimethyl-diamantane | 1.710 | 2.784 | 0.400 |
| 1-Methyl-diamantane | 3.343 | 5.664 | 0.624 |
| 2,4-Dimethyl-diamantane | 2.078 | 3.611 | 0.395 |
| 1,4-dimethyl diamantane | 2.563 | 4.509 | 0.406 |
| 1,4,9-trimethyl diamantane | 1.103 | 1.981 | 0.196 |
| 3-methyl diamantane | 2.384 | 4.241 | 0.359 |
| 4,8-Dimethyl diamantane | 1.618 | 2.970 | 0.195 |
| 4-Ethyl-diamantane | 0.584 | 1.206 | 0.043 |
| Other diamantanes | 16.597 | 34.282 | 1.017 |
| Total diamantanes | 41.292 | 75.146 | 6.499 |
| Triamantane | 1.175 | 2.608 | 0.017 |
| 9-methyl triamantane | 1.151 | 2.583 | 0.016 |
| 9,15-dimethyl triamantane | 0.233 | 0.521 | |
| 3-Me & 3,9-diMe triamantanes | 0.696 | 1.560 | |
| 7,9-diMe & 3,9,15-triMe triamantanes | 0.489 | 1.136 | |
| 4-Me & 4,9,15-triMe triamantanes | 0.440 | 0.973 | |
| 4,9- & 6,9-dimethyl triamantanes | 0.184 | 0.419 | |
| 5-methyl triamantane | 0.289 | 0.661 | |
| 5,9-methyl triamantane | 0.180 | 0.395 | |
| 8-Me & 5,9,15-triMe triamantanes | 0.244 | 0.585 | |
| 9,14-dimethyl triamantanes | 0.144 | 0.238 | |
| 8,9-dimethyl triamantanes | 0.069 | 0.210 | |
| 16-methyl-,a diMe-& a triMe-triamantanes | 0.366 | 0.837 | |
| 2-methyl triamantane | 0.118 | 0.302 | |
| other triamantanes | 1.857 | 4.402 | |
| Total triamantanes + methyl and dimethyl derivatives | 7.605 | 17.430 | 0.033 |
| iso-tetramantane + A + B | 0.119 | 0.283 | |
| 1-tetramantane | 0.023 | 0.059 | |

TABLE 1-continued

Examples of Useful Diamondoid-Containing Feedstocks (wt. %)

| Compounds | A | B | C |
|---|---|---|---|
| other tetramantanes | 0.139 | 0.410 | |
| Total tetramantane | 0.281 | 0.752 | 0.000 |

¶ This sample contained 6.821% of lower boiling materials.
*Prefixes a-, e-, c-, and t- refer to axial, equatorial, cis-, and trans- relationship of substituents in the same cyclohexane ring bearing the substituents in the diamondoids.

EXAMPLE 1

A distillation was carried out in a ASTM D-2887 distillation unit having a column packed with stainless steel saddles. A two-neck flask was used to allow a flow of nitrogen stream through the material to be distilled. Two thousand grams of a crude diamondoid mixture (represented by the gas chromatograph of FIG. 1) was percolated through activated alumina and charged into the flask. Nitrogen was passed through the material at the beginning of the distillation at 20 CC/Min. It was observed that by simply bubbling nitrogen through the bottom of the liquid, even at room temperature, some low boiling point material was collected in a dry ice-/acetone trap. This low boiling point material was not characterized by diamondoid structure. The remainder of the low boiling point material was collected in the receiver. The combined materials from the dry ice/acetone trap and the receiver constituted the low-boiling pre-adamantane fraction which was co-produced with the diamondoids. After the first fraction, the nitrogen flow was increased to 60 CC/Min. Table 2 summarizes the distillation results.

After the distillation, fractions 5, 6, 7, 8, and 9 were combined. Fractions 10 and 11 were combined and saved for further distillation with similar mixtures from additional distillations.

EXAMPLE 2

This example illustrates the method of obtaining the fraction containing triamantanes and tetramantanes. Distillation residue accumulated from five similar distillations as described in Example 1 (1789 grams) was charged to the same distillation unit as described in Example 1. The mixture contained 3.2% adamantanes, 62.3% diamantanes, 34.5% triamantanes+tetramantanes. The distillation of this mixture to separate the adamantanes and diamantanes from the triamantanes and tetramantanes is described in Table 3.

TABLE 2

Distillation of Normally Liquid Diamondoid: Mixture Conditions and Products

| Fr. | Reflux Ratio | Head, °C. | Column, °C. Bottom | Column, °C. Top | Pot °C. | mmHg | Prod. Composition, % Pre-Ad | Ad | Di | Tri + Tetra | Wt., gm |
|---|---|---|---|---|---|---|---|---|---|---|---|
| 1. | 8:1 | 23–24 | 28–29 | 23–24 | 140–190 | atm. | 99 | 1 | 0 | 0 | 114.0 |
| 2. | 8:1 | 42 | 68 | 61 | 210 | atm. | 13.1 | 86.9 | 0 | 0 | 19.1 |
| 3. | 8:1 | 186 | 222 | 215 | 248 | atm. | 33.2 | 66.8 | 0 | 0 | 4.5 |
| 4. | 8:1 | 193 | 225 | 216 | 249 | atm. | 16.3 | 83.1 | 0 | 0 | 13.1 |

(Adamantane crystals condensed at the top of condenser and take-off arm. The solid was melted and collected.
Pure adamantane was obtained by recrystallization from heptane.)

| | | | | | | | | | | | |
|---|---|---|---|---|---|---|---|---|---|---|---|
| 5. | 8:1 | 140 | 231 | 217 | 249 | atm. | 1.5 | 98.5 | 0 | 0 | 207.0 |
| 6. | 8:1 | 144 | 232 | 218 | 249 | atm. | 0.1 | 99.1 | 0.8 | 0 | 192.8 |

(cooled down the system. Started vacuum distillation.)

| | | | | | | | | | | | |
|---|---|---|---|---|---|---|---|---|---|---|---|
| 7. | 8:1 | 39 | 100 | 98 | 100 | 0.3 | 0 | 100 | 0 | 0 | 113.7 |
| 8. | 8:1 | 42 | 100 | 100 | 100 | 0.3 | 0 | 99.7 | 0.3 | 0 | 34.5 |
| 9. | 25:1 | 58 | 119 | 114 | 119 | 0.3 | 0 | 97.6 | 2.4 | 0 | 292.4 |

(Diamantane crystals condensed at the top of condenser and take-off arm. The solid was melted and collected.
Pure diamantane was obtained by recrystallization from heptane.)

| | | | | | | | | | | | |
|---|---|---|---|---|---|---|---|---|---|---|---|
| 10. | 25:1 | 67 | 130 | 125 | 139 | 0.25 | 0 | 57.9 | 42.1 | 0 | 31.6 |
| 11. | 25:1 | 74 | 137 | 130 | 140 | 0.15 | 0 | 35.2 | 64.8 | 0 | 85.4 |

TABLE 2-continued

Distillation of Normally Liquid Diamondoid: Mixture Conditions and Products

| Fr. | Reflux Ratio | Head, °C. | Column, Bottom | Column, Top | Pot °C. | mmHg | Prod. Composition, % Pre-Ad | Ad | Di | Tri + Tetra | Wt., gm |
|-----|--------------|-----------|----------------|-------------|---------|------|------|------|------|-------------|---------|
| 12. | 25:1 | 89 | 156 | 150 | 160 | 0.35 | 0 | 0.6 | 96.8 | 2.6 | 462.6 |

(The pot material, containing diamantanes, triamantanes and tetramantanes, was collected to be combined with similar pot materials from additional distillations to further separate the diamantanes from the triamantanes and tetramantanes as described in Example II.)

TABLE 3

Isolation of Triamantanes - Tetramantanes Fraction and Triamantane Component

| Fr. | Reflux Ratio | Head, °C. | Column, Bottom | Column, Top | Pot °C. | mmHg | Prod. Composition, % Ad | Di | Tri + Tetra | Wt., gm |
|-----|--------------|-----------|----------------|-------------|---------|------|------|------|-------------|---------|

(The mixture was under total reflux at 0.5 mm Hg and 125 C. pot temperature for 12.5 hours.)

| Fr. | Reflux Ratio | Head, °C. | Column, Bottom | Column, Top | Pot °C. | mmHg | Ad | Di | Tri + Tetra | Wt., gm |
|-----|--------------|-----------|----------------|-------------|---------|------|------|------|-------------|---------|
| 1. | 3:1 | 59 | 101 | 97 | 124 | 0.5 | 97.4 | 2.6 | 0 | 18.6 |
| 2. | 3:1 | 78 | 113 | 110 | 138 | 0.5 | 90.8 | 9.2 | 0 | 13.8 |

(Solid diamantane was collected.)

| Fr. | Reflux Ratio | Head, °C. | Column, Bottom | Column, Top | Pot °C. | mmHg | Ad | Di | Tri + Tetra | Wt., gm |
|-----|--------------|-----------|----------------|-------------|---------|------|------|------|-------------|---------|
| 3. | 3:1 | 82 | 123 | 118 | 137 | 0.5 | 9.7 | 90.3 | 0 | 38.3 |
| 4. | 3:1 | 89 | 124 | 120 | 138 | 0.5 | 4.4 | 95.6 | 0 | 141.2 |
| 5. | 6:1 | 83 | 128 | 120 | 145 | 0.4 | 3.8 | 96.2 | 0 | 275.2 |
| 6. | 8:1 | 91 | 111 | 108 | 154 | 0.5 | 2.3 | 97.7 | 0 | 324.6 |
| 7. | 8:1 | 100 | 111 | 108 | 168 | 0.5 | 0 | 99.9 | 0.1 | 236.3 |
| 8. | 8:1 | 91 | 111 | 107 | 164 | 0.35 | 0 | 99.6 | 0.4 | 69.3 |
| 9. | 8:1 | 93 | 106 | 107 | 167 | 0.35 | 0 | 80.5 | 13.7 | 44.4 |

(Triamantane crystals were collected at the take-off, and subsequently purified by recrystallization from heptane.)

| Fr. | | | | | | | Ad | Di | Tri + Tetra | Wt., gm |
|-----|--|--|--|--|--|--|------|------|-------------|---------|
| 10. | | | Pot material | | | | 0 | 0.6 | 99.4 | 625.5 |

(The pot material was yellowish and viscous, 8.09 cS at 100 C. The material was then treated with a mixture of activated alumina (97%) and charcoal (3%). The activated alumina/charcoal treatment produced a virtually colorless product.

EXAMPLES 3 AND 4

Examples 3 and 4 illustrate separation and isolation procedures of diamondoids containing high percentage of solids.

EXAMPLE 3

A diamondoid mixture was recovered from a natural gas field according to the procedure taught in U.S. Pat. No. 5,120,899 to Chen and Wentzek. The diamondoid mixture contained ~10% solid material at room temperature. The solid material, after recrystallization from heptane, was identified to be pure diamantane.

Distillation of the sample diamondoid mixture was attempted three times in the ASTM D-2887 distillation unit described above. Adamantane sublimed even at room temperature under a vacuum of ~1mm Hg. Adamantane was followed by liquid alkyl substituted adamantanes. However, when the diamantane started to sublime, the take-off, the condenser (although jacketed by hot ethylene glycol), and the pathway to the receiver were plugged firmly with diamantane. Unlike the condensed adamantane, the diamantane could not be unplugged by using a heat gun, therefore, the distillation had to be stopped. The diamantane was removed by disassembling the unit and washing the clogged parts with hot heptane.

EXAMPLE 4

In Example 4, the diamondoid mixture of Example 3 was separated first by short-path distillation to the adamantanes, diamantanes+triamantanes; followed by isolation of crystalline adamantane and diamantane from each fraction; then followed by distillation of the remainder liquid as described in Examples 1 and 2. Triamantane was isolated at the end of the distillation as described in Example 2.

EXAMPLE 5

Example 5 demonstrates short-path distillation in a Kugelrohr apparatus. A solids-containing diamondoid mixture (1135 gm) was charged into the distillation pot of a 3-liter Kugelrohr apparatus. The receiver was cooled in a Dry ice/acetone mixture. A vacuum of 0.7 mm Hg was applied. While the apparatus was rotated the pot was heated to 30° C. After 5.5 hours, 649.7 gm of material had been collected in the receiver, and 484.2 gm material remained in the pot. The material in the receiver contained 99% adamantanes and 1% diamantanes. The pot material contained 90% diamantanes+triamantanes and 10% adamantanes.

EXAMPLE 6

The fraction of adamantanes recovered in Example 5 contained a small amount of solids. It was charged into a sublimator, or a distillation unit which was equipped with a large-bore take-off. At a pot temperature of 89° C. and a vacuum of 11.6 mm Hg solid adamantane was obtained as the product. The solid adamantane was followed by clear liquid adamantanes if the distillation was continued. The adamantane was further purified by recrystallization from heptane.

The fraction of diamantanes obtained in Example 5 contained a large amount of solids (bottom ⅓ of the material). The solids were separated by filtration. After recrystallization from heptane, the solids were identified to be pure diamantane. The filtrate was combined with the liquid from the adamantanes and/or from other short-path distillations for further separation by distillation.

EXAMPLE 7

The liquid diamondoids were combined and distilled as described in Examples 1 and 2. The conditions were similar to those described. The product distillate was continuously monitored during the distillation by GC analysis to obtain clean-cut fractions. Fractions of similar compositions were combined after the distillation. Additional smaller amounts of adamantane and diamantane were isolated during the distillation. Triamantane was isolated and recrystallized as described in Example 2.

EXAMPLES 8–10

Examples 8–10 illustrate diamondoid feedstocks useful in the present invention. Examples 8 and 9 contain more than 50 weight percent of diamondoid compounds which are typically solid under ambient conditions. The feedstocks of Examples 8 and 9 are preferably first purified in the short-path distillation step of the invention, prior to the multistage distillation steps of the invention. Alternatively, feedstocks such as those described in Examples 8 and 9 may be filtered at ambient or lower temperature to remove solids.

Example 10 illustrates a diamondoid feedstock containing less than about 25 weight percent of diamondoids which are typically solid under ambient conditions. The solids content of the feedstock shown in Example 10 is low enough that the optional short-path distillation step is not required.

TABLE 4

Comparison of Sample Diamondoid Feedstocks

| Component | Example No. 8 | Example No. 9 | Example No. 10 | |
|---|---|---|---|---|
| | Composition, Weight Percent | | | |
| Adamantane | 17.08 | 13.24 | 2.96 | * |
| 1-Methyladamantane | 26.54 | 22.77 | 11.43 | * |
| 1,3-Dimethyladamantane | 16.40 | 13.61 | 12.00 | |
| 1,3,5-Trimethyladamantane | 3.51 | 3.02 | 4.46 | |
| Other Adamantanes | 3.21 | 4.69 | 47.87 | |
| Diamantane | 16.17 | 15.71 | 2.27 | * |
| 4-Methyldiamantane | 7.03 | 8.53 | 2.17 | |
| 1-Methyldiamantane | 2.65 | 1.25 | 0.81 | |
| other Diamantanes | 3.06 | 12.17 | 77.13 | |
| Triamantane | 2.74 | 2.73 | 0.98 | * |
| 9-Methyltriamantane | 1.31 | 1.60 | 1.22 | * |
| Other Triamantanes | 0.30 | 0.68 | 2.67 | * |
| Total solids and likely solids under ambient conditions | 63.84 | 56.73 | 21.53 | |

*Typically solid under ambient conditions.

Changes and modifications in the specifically described embodiments can be carried out without departing from the scope of the invention which is intended to be limited only by the scope of the appended claims.

What is claimed is:

1. A method for separating high purity diamondoid fractions from a mixture of diamondoid compounds comprising the sequential steps of:
   (a) providing a feed mixture of diamondoid compounds which contains at least 25 weight percent of diamondoid compounds which are normally solid under ambient conditions and which feed mixture further comprises at least about 40 total weight percent substituted and unsubstituted adamantane, at least about 30 total weight percent substituted and unsubstituted diamantane, and at least about 5 total weight percent substituted and unsubstituted triamantane;
   (b) distilling an overhead fraction from said feed mixture of diamondoid compounds in the absence of reflux such that the freeze point of said overhead fraction is higher than the freeze point of said feed mixture;
   (c) cooling said overhead fraction to a temperature above the freeze point of said feed mixture;
   (d) recovering unsubstituted diamondoid solids from said overhead fraction at a purity of at least about 90 weight percent; and
   (e) distilling said overhead fraction of step (d) with reflux to recover substituted diamondoids.

2. The method of claim 1 wherein said method further comprises at least one filtration step at temperature less than or equal to ambient.

3. A method for separating high purity diamondoid fractions from a mixture of diamondoid compounds comprising the steps of:
   (a) providing a feed mixture of diamondoid compounds which contains at least 25 weight percent of diamondoid compounds which are normally solid under ambient conditions and which feed mixture further comprises unsubstituted adamantane, unsubstituted diamantane, unsubstituted triamantane, and substituted diamondoid compounds;
   (b) distilling a first overhead fraction from said feed mixture in the absence of reflux, said first overhead fraction characterized by an average carbon number which is lower than the average carbon number of said feed mixture, wherein said first overhead fraction is further characterized by a higher freeze point than said feed mixture;
   (c) cooling said first overhead fraction to recover unsubstituted adamantane from said cooled first overhead fraction in purity of at least about 90 weight percent;
   (d) continuing said distillation in the absence of reflux to provide a second overhead fraction which upon cooling becomes a liquid and contains predominately a mixture of substituted adamantanes with each component having a higher carbon number than the unsubstituted adamantane and the mixture having a substantially lower freezing point than unsubstituted adamantane;
   (e) distilling said feed mixture in the absence of reflux to provide a third overhead fraction, said third overhead fraction characterized by an average carbon number which is lower than the average carbon number of said feed mixture, wherein said third overhead fraction is further characterized by a higher freeze point than said feed mixture;
   (f) cooling said third overhead fraction to recover unsubstituted diamantane from said cooled third overhead fraction in purity of at least about 90 weight percent;
   (g) continuing said distillation in the absence of reflux to provide a fourth overhead fraction which upon cooling becomes a liquid and contains predominately a mixture of substituted diamantanes with each component of said mixture of substituted diamantanes having a higher carbon number than the unsubstituted diamantane and said mixture of substituted diamantanes having a substantially lower freezing point than unsubstituted diamantane;
   (h) distilling a fifth fraction from said feed mixture in the absence of reflux, said fifth overhead fraction characterized by an average carbon number which is lower than the average carbon number of said feed mixture, wherein said fifth overhead fraction is further characterized by a higher freeze point than said feed mixture;

(i) cooling said fifth overhead fraction to recover unsubstituted triamantane from said cooled fifth overhead stream in purity of at least about 90 weight percent;

(j) recovering pot material containing a major amount of substituted triamantane and minor amounts of tetramantane and pentamantane; and (k) distilling the liquid fractions recovered from steps (c) through (j) with reflux to recovered substituted diamondoid compounds.

4. The method of claim 3 wherein said method further comprises at least one filtration step at temperature less than or equal to ambient.

* * * * *